United States Patent [19]
Jimison et al.

[11] Patent Number: 5,439,355
[45] Date of Patent: Aug. 8, 1995

[54] METHOD AND APPARATUS TO TEST FOR VALVE LEAKAGE IN A PUMP ASSEMBLY

[75] Inventors: Walter L. Jimison, Palo Alto; Craig S. Barker, San Carlos; Marc R. Bunyard, Milipitas, all of Calif.

[73] Assignee: Abbott Laboratories, Abbott Park, Ill.

[21] Appl. No.: 147,154

[22] Filed: Nov. 3, 1993

[51] Int. Cl.⁶ .............................................. F04B 21/02
[52] U.S. Cl. ............................................ 417/63; 73/40
[58] Field of Search ..................... 417/63, 9; 73/40, 46

[56] References Cited

U.S. PATENT DOCUMENTS

| | | | |
|---|---|---|---|
| 4,811,252 | 3/1989 | Furuse | 73/40 |
| 4,818,186 | 4/1989 | Pastrone et al. | 417/63 |
| 4,850,807 | 7/1989 | Frantz | 417/63 |
| 5,000,664 | 3/1991 | Lawless et al. | 417/63 |
| 5,336,053 | 8/1994 | Wynkoop | 73/40 |

*Primary Examiner*—Richard A. Berisch
*Assistant Examiner*—Charles G. Freay
*Attorney, Agent, or Firm*—Christensen, O'Connor, Johnson & Kindness

[57] ABSTRACT

A method and apparatus for determining leakage, particularly of valves, in a pump assembly. A pump assembly (20) includes a primary valve (34) and a secondary valve (36), which may be selectively activated to control the source of fluid input to the pump assembly. The pump assembly also includes an inlet valve (42) and an outlet valve (50) disposed on each side of the pumping chamber (46). Downstream of the outlet valve is disposed a pressure sensor (54), which produces a signal indicative of the pressure of fluid within the pump assembly at that point. Leakage in the inlet or outlet valves is detected in the inlet or outlet valves by filling the pumping chamber with fluid, closing the inlet and outlet valves, and equalizing the pressure in the pump assembly distal to the inlet valve. After the pressure has been equalized, the outlet valve is opened and a reference pulse is determined as a function of the signal produced by the pressure sensor. The outlet valve is then closed and at least a partial pumping cycle is effected to pressurize fluid in the pumping chamber. The outlet valve is opened and a pressure pulse should propagate down the delivery passage from the pumping chamber. If the difference between the magnitude of the pressure pulse and that of the reference pulse is less than a predetermined value, either the inlet or outlet valve has leaked. The primary and secondary valves are checked for leakage in much the same manner.

39 Claims, 6 Drawing Sheets

METHOD AND APPARATUS TO TEST FOR VALVE LEAKAGE IN A PUMP ASSEMBLY

FIELD OF THE INVENTION

This invention generally relates to a pump assembly including a plurality of valves, and particularly relates to apparatus and a method for detecting leakage in any of the valves.

BACKGROUND OF THE INVENTION

Disposable pump cassettes are frequently employed to infuse medicinal fluids into a patient. As described in U.S. Pat. Nos. 4,818,186 and 5,000,664, one type of disposable cassette includes a plastic housing having a front and a rear portion, between which an integral elastic member is encapsulated. The housing has a plurality of ports through which rod-like actuators of a pump drive mechanism interact with the elastomeric membrane to control fluid flow through the cassette housing. A pump plunger on the drive unit displaces the membrane to pressurize liquid trapped in a pumping chamber formed between the membrane and the back of the housing. Similarly, rod-like actuators extend from the drive unit through ports in the housing, pressing against the membrane to interrupt fluid flow through valve passages formed in the back of the housing. A microprocessor in the pump drive controls the pump plunger and rod-like actuators to effect a desired rate of delivery of medicinal fluids to the patient, and in some units, is capable of selecting between a plurality of different sources by opening an appropriate selector valve in the cassette.

Selection of the source fluid and pumping rate or volume are normally determined by an operator programming the pump drive in response to a display prompt. Significant leakage through the valves in the pump cassette can create a potentially harmful variation from the programmed value in the quantity of medication actually delivered to a patient, or in the case of a leaky selector valve, may allow a medicinal fluid to enter the pump cassette when infusion of the fluid into the patient is not desired. Leakage of the valves is difficult or impossible to detect by visual inspection, and may occur after the cassette was originally inspected for leaks during its manufacture. In view of the potential harm to the patient should significant leakage go undetected, there is a clear justification for evaluating the leakage integrity of all valves when cassette is first used to administer drugs, and perhaps at periodic intervals thereafter, e.g., each time that the pump is energized.

Apparatus and a method for detecting valve leakage in a pump cassette are disclosed in U.S. Pat. No. 5,000,664. The cassette disclosed in this reference includes a primary valve and a secondary valve that are selectively activated to control the source of fluid input to the cassette. The cassette also includes an inlet valve and an outlet valve disposed on each side of a pumping chamber. Downstream of the outlet valve is disposed a pressure sensor, which produces a signal indicative of the pressure of fluid within the cassette at that point. Leakage in the inlet or outlet valves is detected by closing both valves, pressurizing fluid in the pumping chamber for a predetermined period of time, and then opening the outlet valve. If a pressure pulse having an amplitude less than a predetermined level is detected downstream of the outlet valve when it is opened, either the inlet or outlet valve has leaked. The primary and secondary valves are checked for leakage by pressurizing fluid trapped in the cassette, delaying for a period of time before closing the inlet valve, and then, opening the outlet valve to detect a pressure pulse propagating downstream of the outlet valve, using the pressure sensor. If a pressure pulse of less than the predetermined magnitude is detected, one of the primary or secondary fluid selectors is leaking. Both tests also detect leakage of other portions of the pump assembly.

The above-described apparatus and algorithm accurately detect valve leakage under most conditions. However, under certain conditions that were previously unrecognized, the above method can fail to detect valve leakage. When the valve leak test is performed on a cassette having valves that do not leak or on a cassette having a defective outlet valve, the results are as expected. However, when the valve leak test is performed on a cassette having a defective inlet valve, at times, a pressure pulse having a magnitude substantially greater than the predetermined minimum magnitude is unexpectedly observed. This false pulse can occur when the inlet valve is leaking because of the pressure head developed by the column of liquid between the pump cassette and the reservoir; the pressure of this head of liquid propagates to the pressure sensor when the outlet valve opens. Thus, for this condition, the defective inlet valve is not detected and leakage is allowed to continue to the detriment of the patient. The present invention ensures that a defective inlet valve is detected.

SUMMARY OF THE INVENTION

In accordance with the present invention, a pump assembly having the capacity to self test for leakage includes a pumping chamber in which liquid is pressurized during a pumping cycle. An inlet valve is operative to periodically interrupt fluid flow into and out of the pumping chamber, with respect to a source of the fluid that is disposed upstream of the inlet valve. Fluid flow into and out from the pumping chamber through a delivery passage is controlled by an outlet valve, which periodically interrupts the fluid flow when the pump assembly is operating to pump fluid.

Downstream of the outlet valve is disposed a pressure sensor that senses the pressure of fluid in the delivery passage and produces a signal indicative of that pressure. Control means are included for controlling the pumping cycle and include self test means that are connected to receive the signal produced by the pressure sensor. The self test means are operative to fill the pumping chamber with fluid, close the inlet and outlet valves, and equalize the pressure in the pump assembly distal to the inlet valve. After the pressure has been equalized, the outlet valve is opened, and a reference pulse is determined as a function of the signal produced by the pressure sensor when the outlet valve is opened. The self test means are then operative to effect at least a partial pumping cycle to pressurize fluid in the pumping chamber. After a predetermined time interval, the self test means opens the outlet valve to determine whether the pump assembly has leaked as a function of the reference pulse and the signal produced by the pressure sensor after the outlet valve is opened following pressurization of the pumping chamber.

When the outlet valve is opened after the fluid in the pumping chamber is pressurized, a pressure pulse should propagate down the delivery passage from the pumping chamber. If the difference between the magnitude of the pressure pulse and that of the reference pulse is less than a predetermined minimum value, the self test means are operative to detect that unacceptable leakage from a volume of fluid nominally trapped between the inlet and outlet valves has occurred. Preferably, the self test means repetitively test for leakage and determine that the pump assembly is leaking only if a predetermined number of such tests indicate leakage.

The pump assembly may include selector valve means, disposed upstream of the inlet valve and connected in fluid communication therewith by an inlet passage. The selector valve means select at least one inlet port from among a plurality of inlet ports on the pump assembly for liquid communication with the inlet valve and pumping chamber.

Detection of leakage from a volume of fluid nominally trapped between the selector valve means and the outlet valve is accomplished by the self test means as follows. The inlet passage and pumping chamber are filled with fluid, the selector valve means and the outlet valve are closed, and a partial equalization of the pressure of the fluid distal to the selector valve means is effected. The outlet valve is then opened and a reference pulse is determined as a function of the signal produced by the pressure sensor when the outlet valve is opened. The self test means are then operative to effect at least a partial pumping cycle to pressurize fluid in the inlet passage and the pumping chamber. After a second predetermined time interval, the self test means open the outlet valve, and determines if the selector valve means have leaked as a function of the reference pulse and the signal produced by the pressure sensor after the outlet valve is opened. If the difference between the magnitude of the pressure pulse propagating down the delivery passage after pressurization and the magnitude of the reference pulse is less than a predetermined value, the self test means are operative to detect a leak in the selector valve means.

A method including steps generally consistent with the functions implemented by the elements of the apparatus described above represents a further aspect of this invention.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
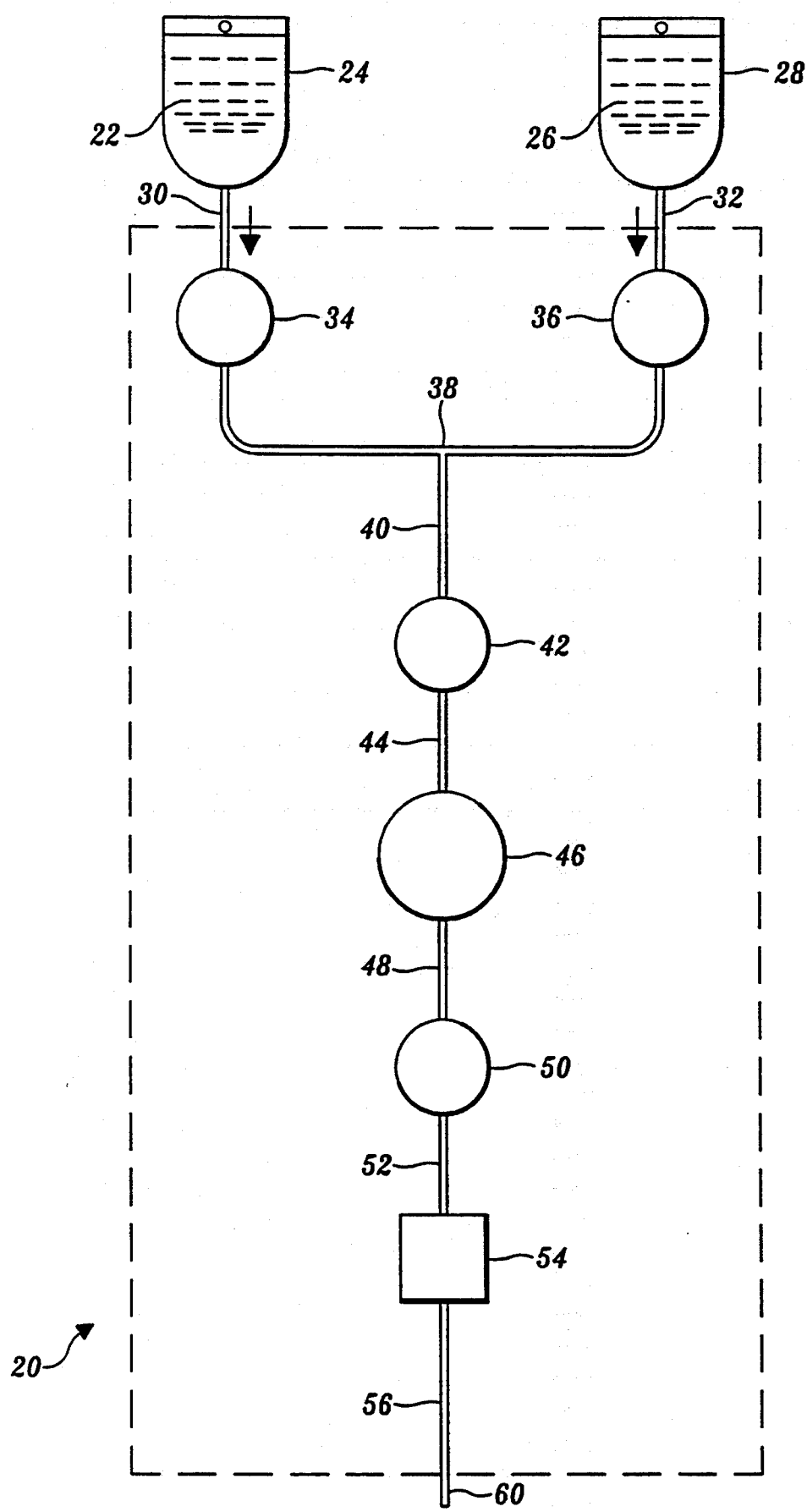
FIG. 1 schematically illustrates the flow path of a liquid through a pump assembly periodically employing a valve leakage test.

A flow diagram for a pump apparatus 20 used to administer liquids intravenously to a patient is shown schematically in FIG. 1. Pump apparatus 20 selectively pumps a first fluid 22, which is supplied from a reservoir bag 24, or a second fluid 26 supplied from a reservoir bag 28. Both reservoir bags 24 and 28 are typically elevated above pump apparatus 20, so that the first and second fluids freely flow downwardly toward the pump assembly. A supply line 30 connects reservoir bag 24 in fluid communication with the primary valve 34, and similarly, a supply line 32 connects reservoir bag 28 in fluid communication with the secondary valve 36. Primary valve 34 and secondary valve 36 are both disposed within pump assembly 20 and are selectively controlled to permit either the first liquid or the second liquid to enter a manifold line 38, which couples both the primary and secondary valves in fluid communication with an inlet passage 40. The inlet passage is connected in fluid communication with an inlet valve 42. The inlet valve selectively enables fluid flow into a pumping chamber 46 through a passage 44.

A passage 48 connects the outlet of the pumping chamber to an outlet valve 50, which selectively controls fluid flow from pumping chamber 46. The outlet valve is connected through a delivery passage 52 to a pressure sensor 54, and fluid flow continues through a delivery passage 56 to a delivery tube 60.

The pressure sensor produces a signal indicative of the pressure of fluid within delivery passages 52 and 56 and is used to detect leakage from the pump apparatus; to determine if inlet valve 42 or outlet valve 50 is leaking; and to determine whether primary valve 34 or secondary valve 36 is leaking. Pressure sensor 54 is also used to determine if hydrodynamic pressure noise would interfere with the valve leakage test conducted by the pump assembly. Pressure sensor 54 comprises a strain gauge (not separately shown) that is biased to a positive DC voltage level, so that its output signal is able to indicate pressures less than ambient. The strain gauge pressure sensor thus typically produces an AC signal indicative of the pressure levels distal of the outlet valve, and this AC signal varies above and below a DC offset voltage that is equal to the sum of the DC offset provided the device and any DC shift caused by substantially constant pressure in the output line of the pumping device. These two portions of the signal are referred to below, respectively, as its AC and DC components.

From FIG. 1, it will be apparent that a leak in either primary valve 34 or secondary valve 36 could permit either the first or second fluid, respectively, to flow into manifold line 38 when the presence of fluid from the nonselected source is not desired. Such leakage could potentially cause a dangerous amount of medicinal fluid to be injected into a patient if leakage of the primary or secondary selector valve should be undetected. In addition, any leakage through inlet valve 42 or outlet valve 50 or from pump apparatus 20 could either reduce the effective pumping rate of medicinal fluid into a patient, or permit fluid flow through the connected delivery tube 60 when pump apparatus 20 is supposed to be inoperative.

It has been observed that any movement of delivery tube 60 by a patient or by an operator can induce pressure noise in the delivery tube that can affect the signal produced by pressure sensor 54 and interfere with the valve leakage test conducted on inlet valve 42, outlet valve 50, primary valve 34, and secondary valve 36. Because of this hydrodynamic pressure noise, a false alarm indicating valve leakage could issue, interrupting the flow of medicinal fluid to the patient unnecessarily. Alternatively, the hydrodynamic pressure noise could mask an actual valve leakage problem. Such interference could have a potentially harmful effect.

Figure 2:
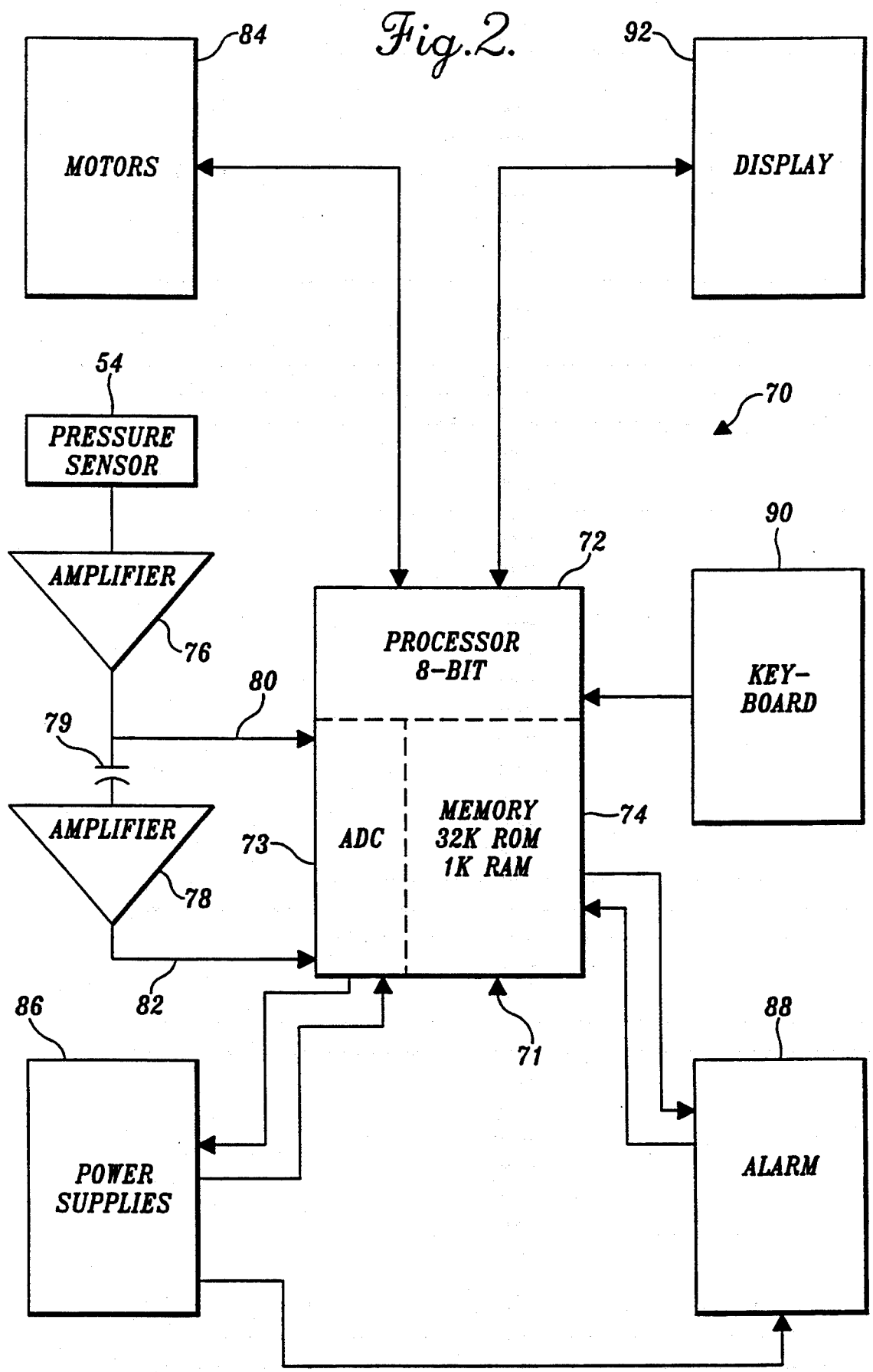
FIG. 2 is an electrical schematic block diagram of a control unit employed in the pump assembly.

Referring now to FIG. 2, a control unit 70 is shown that is used to control pump assembly 20. Control unit 70 contains a microcontroller 71 programmed to effect operation of the pump assembly to deliver a selected one of the first and second medicinal fluids to a patient at a defined rate. Control unit 70 is programmed to conduct leakage tests of the inlet and outlet valves and the primary and secondary valves in accordance with the present invention. In addition, microcontroller 71 is programmed to delay completion of the valve leakage test until hydrodynamic pressure noise has settled. The microcontroller comprises a microprocessor 72 and a memory 74. The memory includes both read only memory (ROM) and random access memory (RAM) (neither separately shown). The microprocessor responds to programmed instructions stored in ROM and maintains values temporarily in RAM of memory 74 associated with microprocessor 72.

A key aspect of the present invention is the use made of output signals from pressure sensor 54. Pressure sensor 54 produces a signal indicative of the pressure of fluid within delivery passage 52 and also produces a signal indicative of hydrodynamic pressure noise. The signal produced by the pressure sensor is amplified by an amplifier 76, which has a relatively low-gain, producing an analog signal 80 that includes both the AC component and DC components discussed above. This low-gain analog signal is input to an analog-to-digital converter (ADC)73 comprising microcontroller 71. The analog signal is also coupled through a capacitor 79 to a second, higher gain amplifier 78, producing a high-gain analog signal 82 including only an AC component. Hydrodynamic pressure noise detected by pressure sensor 54 is better indicated by the high-gain analog signal than it is in low-gain signal 80. The high-gain signal is also received by the ADC within microcontroller 71. The ADC within microcontroller 71 digitizes the low-gain and high-gain analog signals and the resulting digital values corresponding to the analog signals are stored in memory 74. For purposes of simplifying this discussion, the digital value corresponding to the low-gain analog signal is referred to as the "DC-coupled signal" or "low-gain pressure level," and the digital value corresponding to the high-gain analog signal is referred to as the "AC-coupled signal" or "high-gain pressure level."

Also connected to microprocessor 72 are motors 84, a power supply 86, an alarm 88, a keyboard 90, and a display 92. Alarm 88 and display 92, which can selectively produce visual and/or audible alerts, are energized when fault conditions are detected, such as a leak in one of the valves or persistence of hydrodynamic pressure noise. In addition, if a leak is detected in any of the inlet-outlet or primary-secondary valves, or elsewhere in the pump assembly, all valves are closed and operation of pump apparatus 20 is stopped until the condition is corrected by an operator. If all of the valves are not closed and operation of the pump apparatus is not interrupted, undesired fluid flow may continue to the patient.

Stored in ROM within memory 74 are valve leak detection algorithms and an algorithm for delaying the completion of the valve leak detection algorithm until hydrodynamic pressure noise has settled. Further details of the cassette pump and the pumping device in which it is used are disclosed in commonly assigned U.S. Pat. No. 5,000,664, the disclosure and drawings of which are specifically incorporated herein by reference. The algorithm for delaying the completion of the valve leak detection test until hydrodynamic pressure noise has settled is disclosed in commonly assigned U.S. patent application Ser. No. 08/145,003, entitled Method And Apparatus For Minimizing Hydrodynamic Pressure Noise Interference With A Valve Leakage Test, Jimison et al., filed Oct. 29, 1993, pending. The leakage test and the algorithm for dealing with hydrodynamic pressure noise are implemented by microcontroller 71.

The valve leak detection apparatus and method disclosed in U.S. Pat. No. 5,000,664 employs the microcontroller to implement the following prior art valve leakage test, first on the input and output valves, followed by the primary and secondary valves. Leakage in the inlet valve 42 or outlet valve 50 is detected by first closing both primary valve 34 and secondary valve 36. Then, inlet valve 42 and outlet valve 50 are opened to equalize the pressure inside pump assembly 20 and delivery tube 60. Once the pressure is equalized, the inlet and outlet valves are closed, and fluid is pressurized in pumping chamber 46 for a predetermined period of time. The outlet valve is then opened. If a pressure pulse having a magnitude less than a predetermined level is detected by pressure sensor 54 downstream of the outlet valve when it is opened, either the inlet or outlet valve has leaked.

Primary valve 34 and secondary valve 36 are checked for leakage after the test on the inlet and outlet valves is completed. First, after the inlet passages of the pump are filled with fluid and both the primary and secondary valves are closed, the inlet valve is opened and the outlet valve is closed. The fluid then trapped in the pump assembly 20 is pressurized for a period of time before closing inlet valve 42. The outlet valve 50 is then opened and pressure sensor 54 is used to detect a pressure pulse propagating downstream of the outlet valve. If a pressure pulse of less than the predetermined magnitude is detected, one of the primary or secondary valves is leaking. Both tests also detect leakage in other portions of the pump assembly. However, the prior art approach just discussed completely ignores hydrodynamic noise pressure and can fail to detect leakage in inlet valve 42, as noted above in the Background of the Invention. In the current preferred embodiment of the present invention, both of these problems are addressed.

The hydrodynamic noise pressure algorithm disclosed in U.S. patent application Ser. No. 08/145,003 delays completion of the valve leak test described above until hydrodynamic pressure noise in the system has settled. Pressure sensor 54 produces a signal indicative of hydrodynamic pressure level in fluid distal of one of the valves of pump assembly 20. Within the pump assembly, a microcontroller 71 receives the signal produced by the pressure sensor. Memory 74 in the microcontroller stores program instructions that control the microcontroller, causing it to determine whether the valve leakage test should continue. Specifically, the microcontroller responds to the programmed instructions to function as sampling means, testing means, and timing means.

Using the signal produced by pressure sensor 54, microcontroller 71 samples the hydrodynamic pressure noise in the fluid at a frequency that is substantially greater than that of the hydrodynamic pressure noise. The microcontroller then determines if the hydrodynamic noise pressure level is above a predetermined threshold. If so, completion of the valve leakage test is suppressed by microcontroller 71 until the hydrodynamic pressure noise has settled below the predetermined threshold for a predefined time interval. If the hydrodynamic noise pressure level is not above the predetermined threshold, the valve leak test may continue. First, however, in accordance with the present invention, a reference baseline for pressure must be established for use during the completion of the valve leak test. Consequently, a low noise, low-gain pressure base and a low noise, high-gain pressure base are then computed and the valve leak test is allowed to continue. It is important to note that neither of these two reference base pressures were determined in the prior art technique for detecting valve leakage discussed above. If the hydrodynamic pressure noise fails to settle below the predetermined threshold for a predefined time interval, the timing means triggers an alarm.

The prior art valve leak detection method and apparatus described above fails to detect defective valves under certain conditions, even when used only after the hydrodynamic pressure noise has settled. Opening outlet valve 50 even when the inlet valve is not leaking can produce a small dynamic pressure pulse due to the displacement of the elastomeric membrane comprising the valve. However, the combination of a leaking inlet valve and the height of reservoir bags 24 and 28 above the pump assembly 20 may induce an erroneous pressure pulse within the delivery tube that mimics the expected pressure pulse produced in cases where all the valves are not leaking. Specifically, if inlet valve 42 is defective, fluid would not remain pressurized within pumping chamber 46. Therefore, one would expect that a pressure pulse would not propagate downstream of the outlet valve after outlet valve 50 is opened. However, reservoir bags 24 and 28 can be positioned sufficiently high above the pump assembly so that a head pressure is developed in the fluid proximal to the inlet valve. Hence, even though the pressure chamber is not pressurized, a pressure pulse will then propagate distally of the outlet valve when the outlet valve is opened. This pressure pulse is actually indicative of the head pressure at the pump assembly, not the pressure maintained within the pressure chamber. If the reservoir bags are positioned high enough, a pressure pulse will be induced in the delivery tube that is greater than the predetermined level. As a result, following only the procedure of the prior art valve leakage method, a leaking inlet valve will go undetected under these conditions.

Figure 3A:
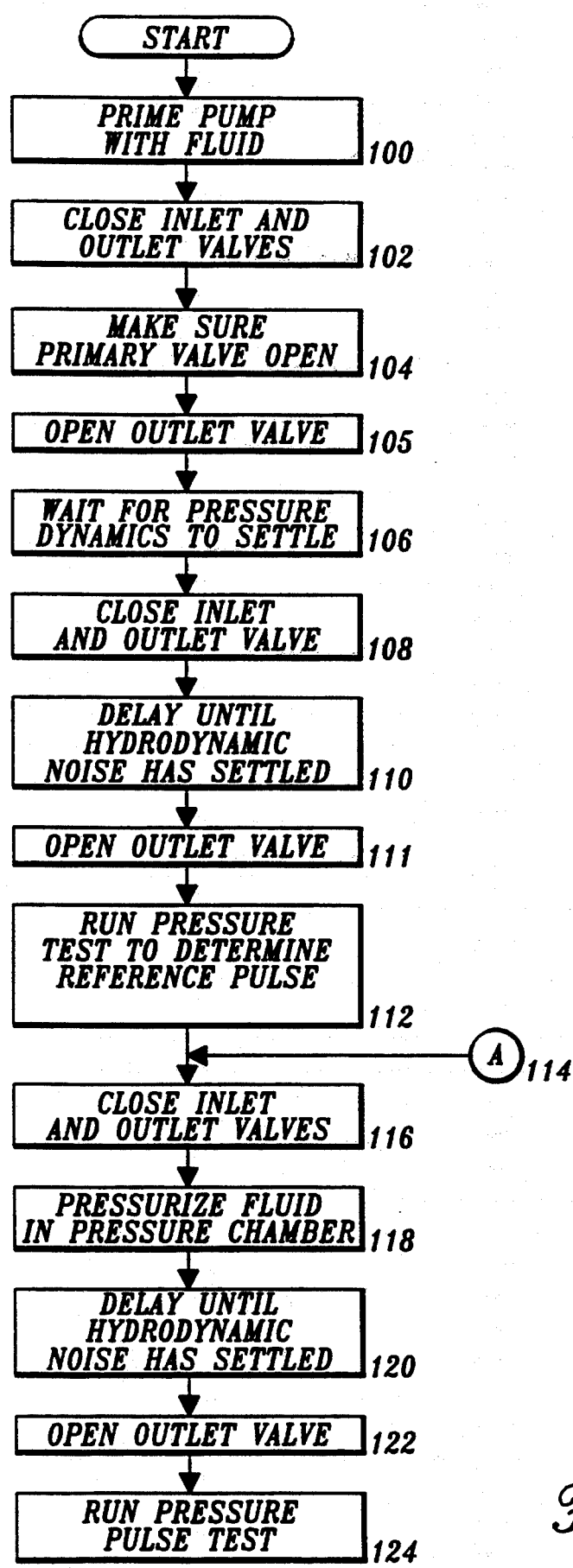
FIGS. 3A, 3B, 3C and 3D are flow charts that illustrate the logic used for testing the input and output valves, and the primary and secondary valves for leaks using the pressure sensor, in accordance with the present invention.

The valve leak detection method of the present invention employs the microcontroller to implement a valve leakage test that overcomes this problem. As shown in FIG. 3A, the algorithm starts and proceeds to a block 100, wherein pump assembly 20 is primed with fluid (by opening either the primary valve or the secondary valve) that is to be delivered to the patient. In a block 102, both the inlet and outlet valves are closed, so that the fluid is trapped within pumping chamber 46 between inlet valve 42 and outlet valve 50.

The pressure in the pump assembly distal to the inlet valve is then equalized. First, in a block 104, the primary (or secondary) valve is checked to ensure that it is open. The logic then proceeds to a block 105, where the outlet valve is opened. In a block 106, the algorithm waits for a predetermined interval of time for pressure dynamics to settle before proceeding to a block 108. In block 108, the inlet and outlet valves are closed once again. After equalization of pressure, the logic proceeds to a block 110, where any further action is delayed until hydrodynamic pressure noise settles. Once the hydrodynamic pressure noise falls beneath a predetermined threshold, the logic continues to a block 111, and outlet valve 50 is opened. When the outlet valve is opened, a dynamic pressure pulse propagates through delivery passage 52, downstream of outlet valve 50, and is sensed by pressure sensor 54. In block 112, the first step in determining the reference pulse is conducted using the dynamic pressure pulse wave in order to obtain a reference pulse that will be used when an actual pressure pulse test in conducted.

Figure 3B:
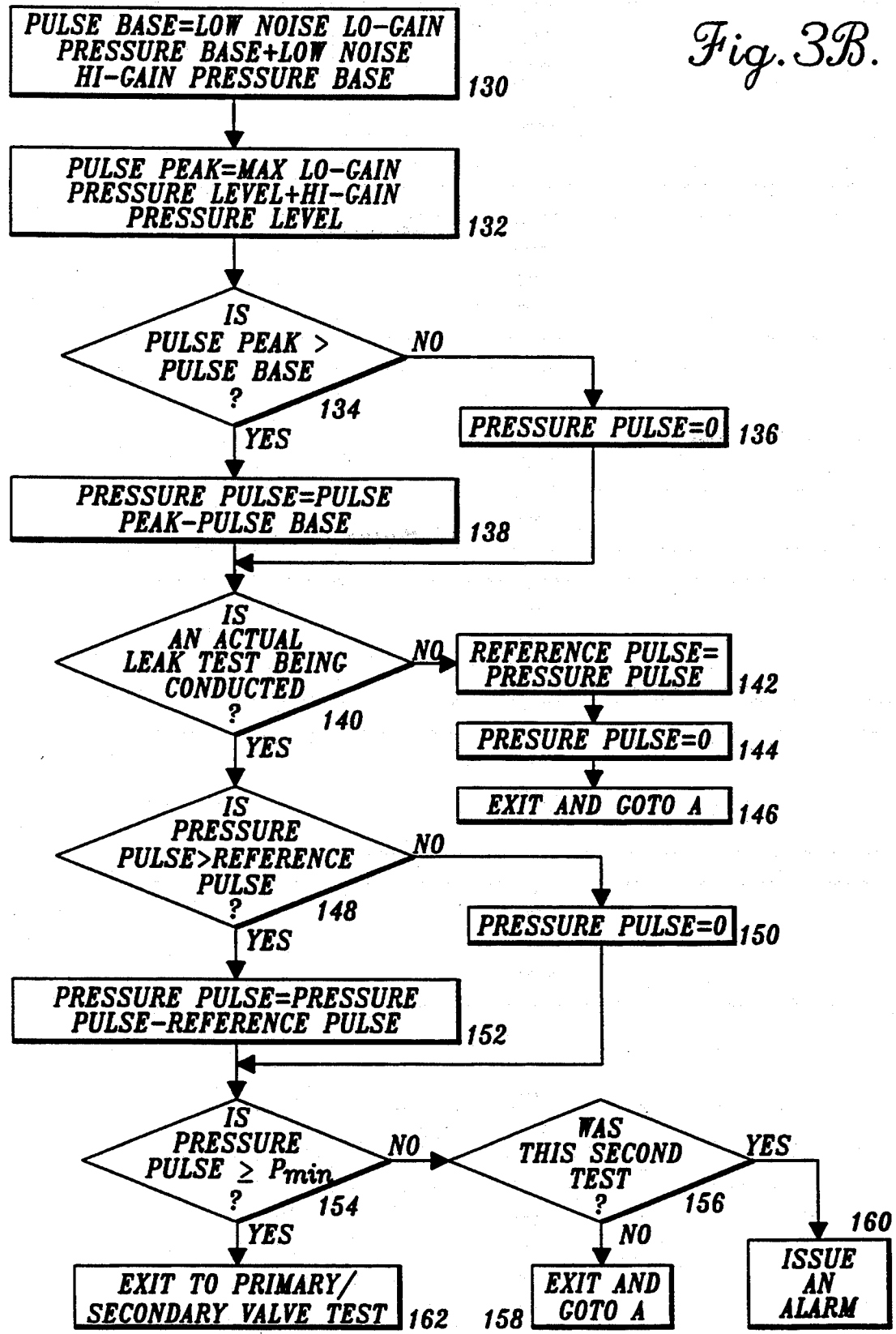

As shown in FIG. 3B, the determination of the reference pulse begins in a block 130, with determining the base value of the pressure pulse, which is the sum of the low noise low-gain pressure base and the low noise high-gain pressure base obtained from the hydrodynamic pressure noise algorithm described above. The logic then proceeds to a block 132, where the peak value of the pressure pulse is determined by adding the maximum low-gain pressure level (magnitude) and the maximum high-gain pressure level (magnitude) obtained from the current pressure pulse. In a decision block 134, the logic determines if the pulse peak is greater than the pulse base. If the results are negative, the logic proceeds to a block 136, where the magnitude of the pressure pulse is set to zero. If the results in decision block 134 are positive, the logic proceeds to a block 138, where the magnitude of the pressure pulse is set to the difference between the pulse peak and the pulse base.

Once the magnitude of the pressure pulse has been determined, the logic proceeds to a decision block 140, to determine if an actual pressure pulse test is being conducted. In the instant case, the reference pulse is being determined in preparation for conducting the actual pressure pulse test, therefore, the results are negative. Consequently, the logic proceeds to a block 142, where the magnitude of reference pulse is set equal to the magnitude of the pressure pulse. Continuing to a block 144, the magnitude of the pressure pulse is then reinitialized to zero. Once the reference pulse has been determined, the logic proceeds to a block 146, to exit the routine used to determine this value, so that an the pressure pulse test can be conducted using the reference pulse value. To conduct the pressure pulse test to determine valve leakage, the logic now returns to point A, located at a block 114 in FIG. 3A.

The logic continues at a block 116 in FIG. 3A, where the inlet and outlet valves are again closed. In a block 118, the fluid in pressure chamber 46 is then pressurized. Continuing to block 120, the valve leakage test is delayed until hydrodynamic pressure noise has settled. Once the hydrodynamic pressure noise level falls below a predetermined threshold, the logic proceeds to a block 122, where the outlet valve is opened again. When outlet valve 46 is opened (and assuming that the outlet valve has not leaked), a dynamic pressure pulse propagates through delivery passage 52, downstream of outlet valve 50, and is sensed by pressure sensor 54. The logic then proceeds to block 124, where an actual pressure pulse test is conducted using the pressure pulse detected after the pumping chamber has been pressurized and outlet valve 50 has been opened.

As shown in FIG. 3B, the actual pressure pulse test begins at block 130 as did the steps used to determine the reference pulse, but using the pressure pulse value produced when the outlet valve is opened after fluid has been pressurized in the pumping chamber. The logic then proceeds through blocks 132 through 138 to decision block 140, where the logic determines if an actual pressure pulse test is being conducted. In this case, the pressure pulse test is being conducted and the reference pulse has already been determined. Therefore, the logic proceeds to a decision block 148, where the logic determines if the magnitude of the pressure pulse is greater than that of the reference pulse. If the result is negative, the logic proceeds to a block 150, where the magnitude of the pressure pulse is set to zero. If the results of the inquiry in decision block 148 are positive, a new magnitude for pressure pulse is determined in a block 152, as the difference between the old magnitude of the pressure pulse and the magnitude of the reference pulse. The logic then proceeds to a block 154, where microcontroller 71 determines if the new magnitude of the pressure pulse is equal or greater than a predetermined value, $P_{min}$. If so, the software logic proceeds to a block 162, and exits the pressure pulse test to begin the valve leak test on the primary and secondary valves.

Assuming that the magnitude of the pressure pulse is less than $P_{min}$ in block 154, the logic in a decision block 156 determines if there has been a previous test of the inlet and outlet valve leak integrity, and if not, the logic repeats the inlet/outlet (I/O) valve leak test, starting at point A in block 114. If the magnitude of the pressure pulse is less than or equal to $P_{min}$ in the second test, the logic proceeds to a block 160, wherein an alarm is effected, comprising either an audible or visual signal to alert the operator that excessive valve leakage has been detected. While determination of I/O valve leakage only depends on the results of two such tests in the preferred embodiment, it may be made to depend on the results of one or more than two consecutive tests.

Figure 3C:
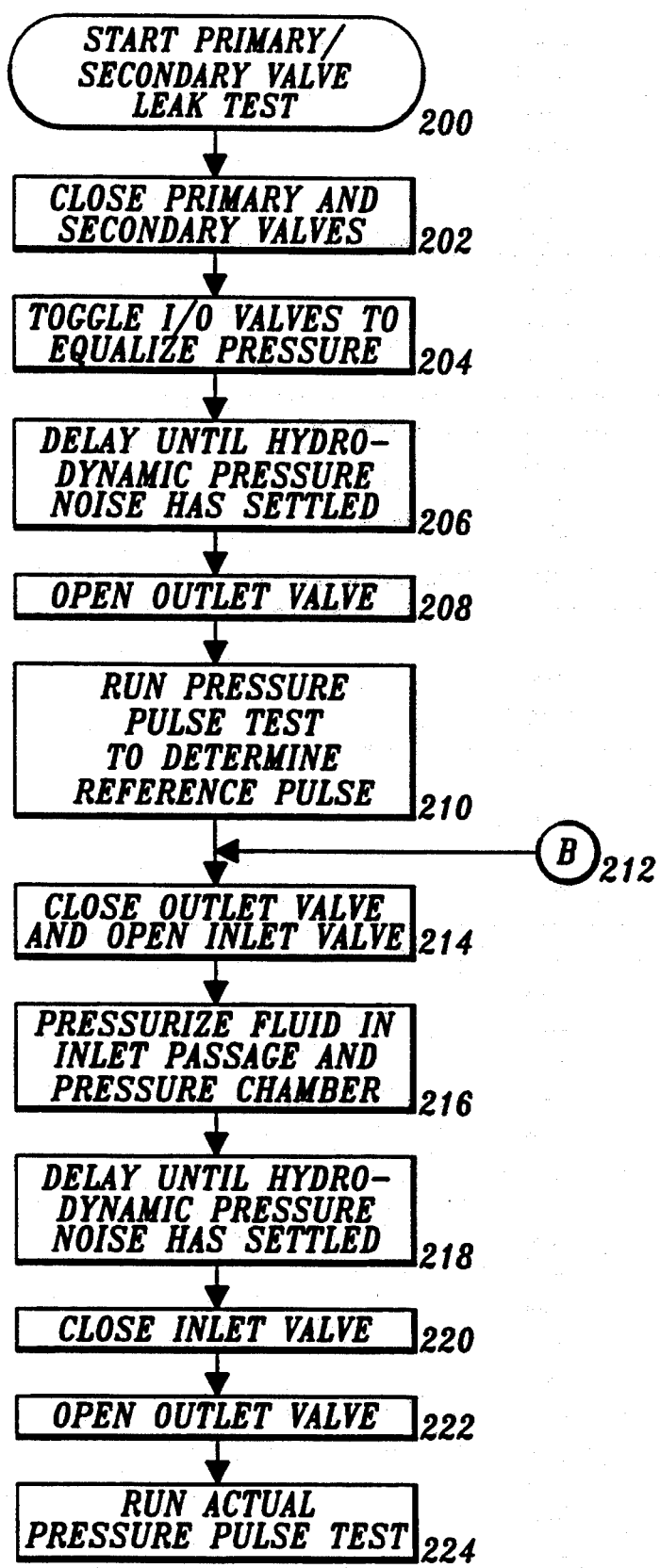

FIG. 3C illustrates the logic used to test primary valve 34 and secondary valve 36 and the portion of the pump assembly 20 between those two valves and outlet valve 50 for leakage integrity as a function of the signal output from pressure sensor 54. This test is similar to that used to test the leakage integrity of inlet valve 42 and outlet valve 50. The logic in FIG. 3C starts with a block 200. From block 200, the logic proceeds to a block 202 in which the primary and secondary valves are closed. In block 204, inlet valve 42 and outlet valve 50 are toggled between their opened and closed conditions through an intermediate state in which they are both closed, to partially equalize internal pressure within pump assembly 20, but distal to the primary and secondary valves. In the preferred embodiment, it is only necessary to toggle the inlet and outlet valves once in order to partially equalize the pressure in the pump assembly. However, the inlet and outlet valves may optionally be toggled several more times in order to ensure equalization of the pressure. After the pressure has been equalized in block 204, no further action is taken until hydrodynamic pressure noise has settled in a block 206. Once hydrodynamic pressure noise has settled below a predetermined threshold, the outlet valve is opened in a block 208. In accordance with a block 210, a test is conducted in order to obtain a reference pressure pulse.

Figure 3D:
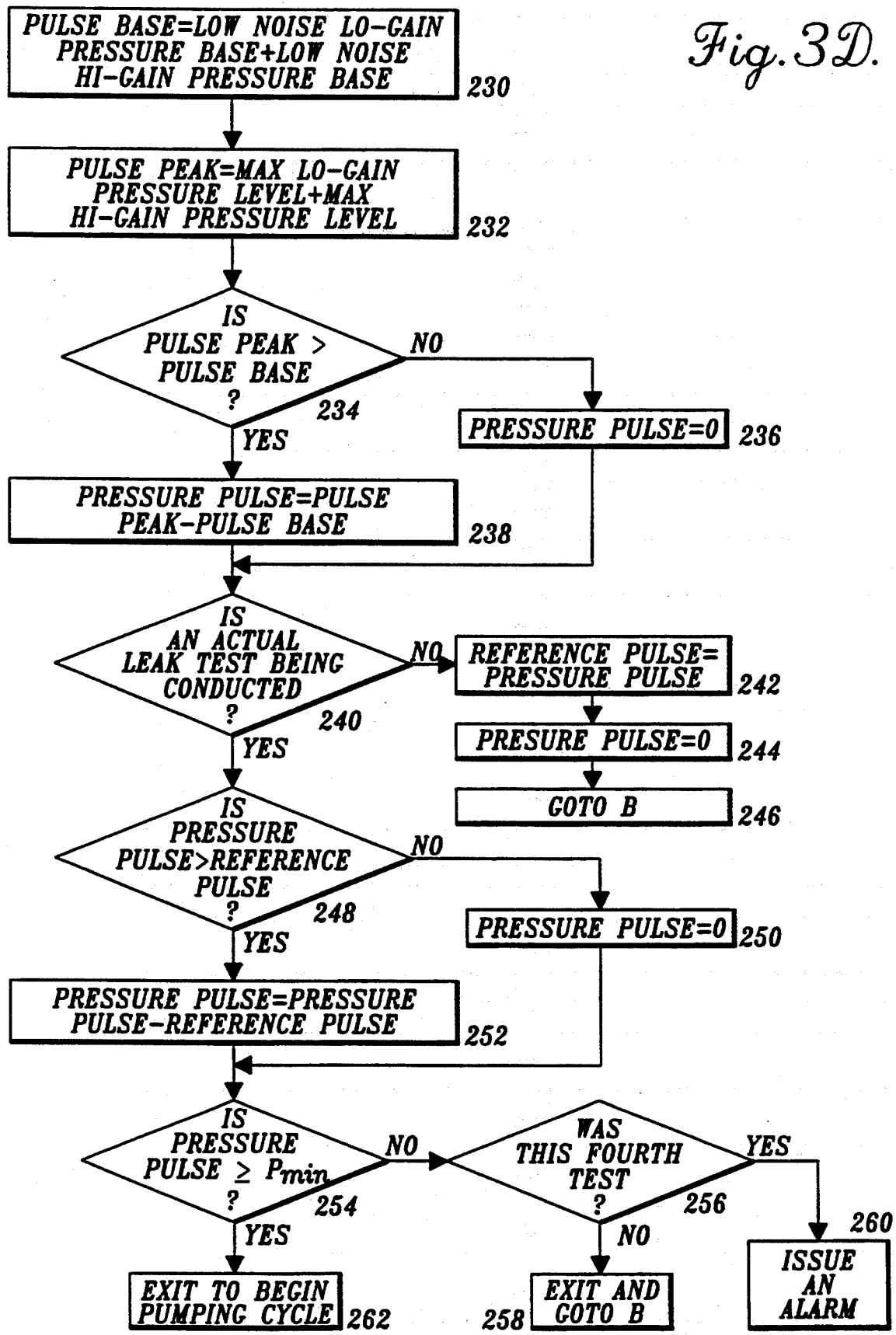

As shown in FIG. 3D, virtually the same steps of a pressure pulse test defined by blocks 230 through 238 are conducted with respect to the primary and secondary valves to determine the reference pressure pulse as were conducted with respect to the inlet and outlet valves. Thus, once a magnitude of a reference pulse is established in either block 236 or 238, the logic exits the pressure pulse test and returns to point B at a block 212 (in FIG. 3C).

Referring back to FIG. 3C, the logic now proceeds to a block 214, where outlet valve 50 is closed and inlet valve 42 is opened. In a block 216, the fluid within pumping chamber 46 and the internal passages of the pump assembly 20 is pressurized back to both primary valve 34 and secondary valve 36, which are closed. Continuing at block 218, no further action is taken until hydrodynamic pressure noise has settled. Once the hydrodynamic pressure noise falls beneath a predetermined threshold, inlet valve 42 and outlet valve 50 are opened in blocks 220 and 222, respectively. The pressure pulse test is then run in a block 224 to detect leakage of the primary or secondary valves, as defined by the steps shown in FIG. 3D.

Again as shown by the steps carried out in blocks 230 through 262 of FIG. 3D, virtually the same pressure pulse test to determine valve or pumping apparatus leakage is conducted with respect to the primary and secondary valves, as was conducted on the inlet and outlet valves in FIG. 3B, with two minor exceptions. First, in a block 262, successful completion of the primary and secondary valve leak test leads to exiting the leakage test algorithm and initiating the pumping cycle.

Second, upon failure to pass the leak test in a block 254, the logic proceeds to a block 256, which determines if this is the fourth time the test has failed (as opposed to the second), and if so, issues an alarm in block 260. If fewer than four tests have indicated a primary valve or secondary valve leak, the logic proceeds to a block 255, where it exits the pressure pulse test and returns to conduct another valve leak test at point B in block 212. Optionally, from one to three, or alternatively, more than four repetitions of the test can instead be conducted before an alarm is initiated.

While the preferred embodiment of the invention has been illustrated and described, it will be appreciated that various changes can be made therein without departing from the spirit and scope of the invention. Accordingly, it is not intended that the scope of the invention be limited by the disclosure of the preferred embodiment. Instead, the invention should be determined entirely by reference to the claims that follow.

The embodiments of the invention in which an exclusive property or privilege is claimed are defined as follows:

1. A pump assembly having the capacity to self test for leakage, comprising:
    (a) a pumping chamber in which a fluid is pressurized during a pumping cycle;
    (b) an inlet valve that periodically interrupts fluid flow into and out of the pumping chamber, with respect to a source of the fluid disposed upstream of the inlet valve;
    (c) an outlet valve that periodically interrupts fluid flow into and out of the pumping chamber, with respect to a delivery passage through which a pressurized fluid flows when the pump assembly is operating to pump the fluid;
    (d) a pressure sensor, disposed downstream of the outlet valve and operative to sense the pressure of the fluid and to produce a signal indicative of that pressure; and (e) control means for controlling the pumping cycle, including self test means connected to receive the signal produced by the pressure sensor, for:
  (i) filling the pumping chamber with fluid;
  (ii) closing the inlet and outlet valves;
  (iii) equalizing pressure in the pump assembly distal to the inlet valve;
  (iv) opening the outlet valve and then determining a reference pulse as a function of the signal produced by the pressure sensor when the outlet valve is opened;
  (v) closing the outlet valve and effecting at least a partial pumping cycle to pressurize fluid in the pumping chamber for a predetermined time interval, and thereafter terminating the pumping cycle;
  (vi) opening the outlet valve after the pumping chamber has been pressurized; and
  (vii) determining whether the pump assembly has leaked, as a function of the reference pulse and the signal produced by the pressure sensor after the outlet valve is opened in section (e)(vi).

2. The pump assembly of claim 1, wherein the self test means are further operative to open the outlet valve in section (e)(iv) after the pressure has been equalized in the pump assembly distal to the inlet valve and hydrodynamic pressure noise has settled.

3. The pump assembly of claim 1, wherein the self test means are further operative to open the outlet valve in section (e)(iv) after the pumping chamber has been pressurized and hydrodynamic pressure noise has settled.

4. The pump assembly of claim 1, wherein said signal produced by the pressure sensor is indicative of a pressure pulse caused by propagation of a pressurized fluid wave down the delivery passage from the pressure chamber when the outlet valve is opened in section (e)(vi).

5. The pump assembly of claim 4, wherein an unacceptable leakage from a volume of fluid nominally trapped between the inlet and outlet valves is detected by the self test means if a difference between a magnitude of the pressure pulse and that of the reference pulse is less than a predetermined value.

6. The pump assembly of claim 1, wherein the control means are further operative to effect an alarm if the self test means determine that the pump assembly has leaked.

7. The pump assembly of claim 6, wherein the self test means are operative to repetitively test for fluid leakage, and to determine that one of the inlet and outlet valves, and the pump assembly is leaking only if a predetermined number of such tests indicate leakage.

8. The pump assembly of claim 1, further comprising selector valve means, disposed upstream of the inlet valve and connected in fluid communication therewith by an inlet passage, for selecting at least one inlet port from among a plurality of inlet ports on the pump assembly for connection to the source supplying the fluid to the inlet valve and pumping chamber.

9. The pump assembly of claim 8, wherein the self test means are further operative to equalize the pressure in the pump assembly distal to the inlet valve by:
  (a) ensuring the selector valve means are open;
  (b) opening the outlet valve; and
  (c) after a predetermined time interval, closing the inlet and outlet valves.

10. The pump assembly of claim 8, wherein the self test means are further operative to detect leakage by:
  (a) filling the inlet passage and pumping chamber with the fluid;
  (b) closing the selector valve means;
  (c) effecting at least a partial equalization of pressure in the pump assembly distal to the selector valve means;
  (d) opening the outlet valve and the determining a reference pulse as a function of the signal produced by the pressure sensor, when the outlet valve is opened;
  (e) closing the outlet valve and effecting at least a partial pumping cycle to pressurize fluid in the inlet passage and in the pumping chamber for a predetermined time interval, then terminating the pumping cycle;
  (f) opening the outlet valve after the inlet passage and the pumping chamber have been pressurized; and
  (g) determining whether the pump assembly has leaked as a function of the reference pulse and the signal produced by the pressure sensor after the outlet valve is opened in section (f).

11. The pump assembly of claim 10, wherein the self test means are further operative to open the outlet valve in section (d) after the pressure has been partially equalized in the pump assembly distal to the selector valve means and hydrodynamic pressure noise has settled.

12. The pump assembly of claim 10, wherein the self test means are further operative to open the outlet valve in step 10(f) after the inlet passage and pumping chamber have been pressurized and hydrodynamic pressure noise has settled.

13. The pump assembly of claim 10, wherein said signal produced by the pressure sensor is indicative of a pressure pulse caused by propagation of a pressurized fluid wave down the delivery passage from the pressure chamber when the outlet valve is opened in section (f).

14. The pump assembly of claim 13, wherein an unacceptable leakage from a volume of fluid nominally trapped between the selector valve means and the inlet valve is detected by the self test means if a difference between a magnitude of the pressure pulse and that of the reference pulse is less than a predetermined value.

15. The pump assembly of claim 10, wherein the self test means are operative to repetitively test for fluid leakage, and to determine if one of the selector valve means and pump assembly is leaking only if a predetermined number of such tests indicate leakage.

16. The pump assembly of claim 10, wherein the control means are further operative to close the inlet valve, outlet valve, and selector valve means and to stop operation of the pump assembly if leakage is detected in at least one of the inlet valves, outlet valves, selector valve means and pump assembly.

17. In a pump assembly including in inlet valve, an outlet valve, a chamber in which fluid is pressurized during a pump cycle, and a pressure sensor disposed downstream of the outlet valve, a method for testing the leak-proof integrity of the pump assembly, comprising the steps of:
  (a) filling the pumping chamber with fluid;
  (b) closing the inlet and outlet valves;
  (c) opening the outlet valve after equalizing pressure in the pump assembly distal to the inlet valve;
  (d) monitoring the fluid pressure downstream of the outlet valve, after it is opened;

(e) determining a reference pressure as a function of said fluid pressure when the outlet valve is opened;

(f) closing the outlet valve and effecting at least a partial pumping cycle to pressurize fluid in the pumping chamber for a predetermined time interval, then terminating the pumping cycle;

(g) opening the outlet valve after the pumping chamber has been pressurized; and (h) determining whether the pump assembly has leaked, as a function of the reference pressure and said fluid pressure, after the outlet valve is opened in step (g).

18. The method of claim 17, wherein the step of equalizing pressure in the pump assembly distal to the inlet valve includes the steps of:

(a) opening the outlet valve; and (b) after a predetermined time interval, closing the inlet and outlet valves.

19. The method of claim 17, wherein the step of opening the outlet valve in step (c) occurs after the pressure has been equalized in the pump assembly distal to the inlet valve and hydrodynamic pressure noise has settled.

20. The method of claim 17, wherein the step of opening the outlet valve in step (g) occurs after the pumping chamber has been pressurized and hydrodynamic pressure noise has settled.

21. The method of claim 17, wherein the step of monitoring includes the step of detecting a pressure pulse propagating downstream of the outlet valve after it is opened in step (g).

22. The method of claim 21, wherein the step of determining the reference pressure includes the step of determining a magnitude of the pressure pulse after the pressure has been equalized in the pump assembly distal to the inlet valve.

23. The method of claim 22, wherein the step of determining whether the pump assembly has leaked includes the steps of:

(a) determining a magnitude of the pressure pulse after the chamber has been pressurized; and (b) determining if a difference between the magnitude of the pressure pulse and that of the reference pressure pulse exceeds a predetermined value, leakage of the fluid from a volume of fluid nominally trapped between the inlet and outlet valve causing the difference to be less than said predetermined value.

24. The method of claim 17, further comprising the step of effecting an alarm if a leak is detected.

25. The method of claim 17, further comprising the step of repeating steps (d) through (h) a plurality of times, wherein step (f) comprises the step of determining whether the pump assembly is leaking as a function of the reference pressure and pressure pulses measured in a plurality of such repetitions.

26. The method of claim 17, wherein the pump assembly further comprises a selection valve, disposed upstream of the inlet valve and connected in fluid communication therewith by an inlet passage, for selecting at least one inlet port from among a plurality of inlet ports on the pump assembly for connection to the source supplying the fluid to the inlet valve and pumping chamber; and wherein the method for testing the leakproof integrity of the pump assembly further comprises the steps of:

(a) filling the inlet passage and pumping chamber with the fluid;

(b) closing the selector valve means and the outlet valve;

(c) effecting at least a partial equalization of pressure in the pump assembly distal to the selector valves;

(d) opening the outlet valve and then determining a reference pulse as a function of the signal produced by the pressure sensor when the outlet valve is opened;

(e) closing the outlet valve and effecting at least a partial pumping cycle to pressurize fluid in the inlet passage and in the pumping chamber for a predetermined time interval, then terminating the pumping cycle;

(f) opening the outlet valve after the inlet passage and the pumping chamber have been pressurized; and (g) determining whether the pump assembly has leaked as a function of the reference pulse and the signal produced by the pressure sensor after the outlet valve is opened in step (f).

27. The method of claim 26, wherein the step of opening the outlet valve in step (d) occurs after the pressure has been partially equalized in the pump assembly distal to the selector valves and hydrodynamic noise pressure has settled.

28. The method of claim 26, wherein the step of opening the outlet valve in step (f) occurs after the inlet passage and pumping chamber have been pressurized and hydrodynamic pressure noise has settled.

29. The method of claim 26, wherein the step of determining the reference pressure incudes the step of determining a magnitude of the pressure pulse after the pressure has been equalized in the pump assembly distal to the selector valves, before the inlet passage and pumping chamber are at least partially pressurized.

30. The method of claim 29, wherein the step of determining whether the pump assembly has leaked includes the steps of:

(a) determining a magnitude of the pressure pulse after the inlet passage and pumping chamber have been pressurized; and (b) determining if a difference between the magnitude of the pressure pulse and that of the reference pulse exceeds a predetermined value, leakage of the fluid from a volume of fluid nominally trapped between the selector valves and the outlet valve causing the difference to be less than the predetermined value.

31. The method of claim 24, further comprising the step of repeating steps (b) through (g) a plurality of times, wherein step (g) comprises the step of determining whether the pump assembly is leaking as a function of the reference pressure and pressure pulses measured in a plurality of such repetitions.

32. The method of claim 24, further comprising the steps off (a) closing the inlet valve, outlet valve and selector valve means; and (b) stopping operation of the pump assembly, if leakage has been detected in at least one of the inlet valves, outlet valves, selector valve means and pump assembly.

33. In a pump assembly having a plurality of valves, including an inlet valve and an outlet valve, and the pumping chamber disposed between the inlet valve and the outlet valve, apparatus to test for leakage of the pump assembly, comprising:

(a) pressure sensing means for producing a signal indicative of the pressure of fluid in a fluid passage downstream of the outlet valve;

(b) reference pulse determining means, connected to receive the signal produced by the pressure sensing means, for determining a reference pulse as a function of the signal produced by the pressure sensing means immediately after the outlet valve is opened, said outlet valve being opened after the pressure of fluid in the pump assembly distal to the inlet valve has been equalized to that distal of the outlet valve; and (c) leak detection means, connected to receive the signal produced by the pressure sensing means, for detecting leakage from the pump assembly as a function of the reference pulse and the signal produced by the pressure sensing means immediately after the outlet valve is opened, said outlet valve being opened after fluid within the pumping chamber has been pressurized for a predetermined interval of time.

34. The apparatus of claim 33, wherein leakage is detected by the leak detection means if the signal produced by the pressure sensing means indicates that a difference between a magnitude of a pulse propagating through the fluid passage after the pumping chamber has been pressurized and the outlet valve is opened, and a magnitude of the reference pulse is less than a predetermined value.

35. The apparatus of claim 33, further comprising means for effecting an alarm when leakage is detected.

36. The apparatus of claim 33, wherein the plurality of valves further include selector valve means for selecting a source of fluid for input to the pumping chamber from among a plurality of inlets to the pump assembly, as determined by the control means, said selector valve means being connected in fluid communication with the inlet valve by an inlet passage.

37. The apparatus of claim 36, wherein the leak detection means are further operative to detect leakage through the selector valve means as a function of the reference pulse and the signal produced by the pressure sensing means when the outlet valve is opened releasing pressurized fluid from the pumping chamber, said liquid having been initially trapped between the selector valve means and the outlet valve and then pressurized.

38. The apparatus of claim 37, wherein leakage is detected by the leak detection means if the signal produced by the pressure sensing means after the fluid is pressurized between the selector valve means and the outlet valve, and the outlet valve is opened indicates that a difference between the magnitude of the said signal and the magnitude of the reference pulse is less than a predetermined value.

39. The apparatus of claim 37, further comprising means for closing the inlet valve, the outlet valve, and selector valve means and stopping operation of the pump assembly if leakage is detected in at least one of the inlet valves, outlet valves, selector valve means and pump assembly.

* * * * *

UNITED STATES PATENT AND TRADEMARK OFFICE
CERTIFICATE OF CORRECTION

PATENT NO. : 5,439,355
DATED : August 8, 1995
INVENTOR(S) : W.L. Jimison et al.

It is certified that error appears in the above-indentified patent and that said Letters Patent is hereby corrected as shown below:

| COLUMN | LINE | |
|---|---|---|
| 5 | 31 | "(ADC)73" should read --(ADC) 73-- |
| 12 (Claim 10, | 9 line 9) | After "and" delete "the" |
| 14 (Claim 32, | 54 line 2) | "off" should read --of:-- |

Signed and Sealed this

Fifth Day of December, 1995

Attest:

BRUCE LEHMAN

Attesting Officer

Commissioner of Patents and Trademarks